United States Patent
Stelter et al.

(10) Patent No.: US 6,420,330 B1
(45) Date of Patent: Jul. 16, 2002

(54) USE OF QUATERNARY CARBOXYLIC ACID ALKANOLAMINE ESTER SALTS AS MICROBICIDE AGENTS

(75) Inventors: Norbert Stelter; Guenter Uphues, both of Monheim (DE)

(73) Assignee: Cognis Deutschland GmbH, Duesseldorf (DE)

( * ) Notice: Subject to any disclaimer, the term of this patent is extended or adjusted under 35 U.S.C. 154(b) by 0 days.

(21) Appl. No.: 09/509,366
(22) PCT Filed: Sep. 15, 1998
(86) PCT No.: PCT/EP98/05840
§ 371 (c)(1),
(2), (4) Date: Nov. 28, 2000
(87) PCT Pub. No.: WO99/15013
PCT Pub. Date: Apr. 1, 1999

(30) Foreign Application Priority Data

Sep. 24, 1997 (DE) .......................................... 197 42 222

(51) Int. Cl.⁷ ................................................. C11D 1/62
(52) U.S. Cl. .................... 510/319; 510/329; 510/518
(58) Field of Search ................................. 510/131, 319, 510/329, 330, 504, 515, 518, 522

(56) References Cited

U.S. PATENT DOCUMENTS

| | | |
|---|---|---|
| 3,910,971 A | 10/1975 | Hunsucker et al. |
| 3,915,867 A | 10/1975 | Kang et al. |
| 4,370,272 A | 1/1983 | Wechsler et al. |
| 4,824,867 A | 4/1989 | Smith et al. |
| 5,536,421 A * | 7/1996 | Hartman et al. ............... 8/137 |

FOREIGN PATENT DOCUMENTS

| | | |
|---|---|---|
| CA | 2044234 | 12/1991 |
| DE | 41 05 536 A1 | 8/1992 |
| EP | 0 059 980 A1 | 9/1982 |
| EP | 0 186 052 A1 | 7/1986 |
| EP | 0 239 910 A2 | 10/1987 |
| EP | 0 293 955 A2 | 12/1988 |
| EP | 0 295 739 A2 | 12/1988 |
| EP | 0 309 052 A2 | 3/1989 |
| EP | 0 461 419 A1 | 12/1991 |
| NL | 1 001 114 C | 3/1997 |

OTHER PUBLICATIONS

Chemical Abstracts, vol. 76, No. 12, Mar. 20, 1972, Columbus, Ohio, US; Abstract No. 61261, Komkov, I. P. et al: "Surface–active quaternary ammonium salts of o–acylcholines", XP002092702, & IZV. VYSSH. Ucheb. Zaved., Khim. Khim. Tekhnol. (1971), 14(9), 1369–73 Coden: Ivukar.

Chemical Abstracts, vol. 106, No. 19, 1987, Columbus, Ohio, US; Abstract No. 155889c, XP002092703, & CS 233 421 A (I. CSIBA et al), Aug. 15, 1986.

Chemical Abstracts, vol. 120, No. 21, 1994, Columbus, Ohio, US; Abstract No. 269666x, XP002092704, & CS 276 206 A (I. CSIBA et al), Apr. 15, 1992.

* cited by examiner

*Primary Examiner*—John Hardee
(74) *Attorney, Agent, or Firm*—John E. Drach; Aaron R. Ettelman

(57) ABSTRACT

A process for destroying or preventing the proliferation of microorganisms involving contacting the microorganisms with a quaternary carboxylic acid alkanolamine ester salt corresponding to formula I:

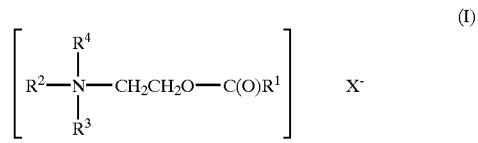

wherein $R^1CO$ is an acyl group having from 2 to 18 carbon atoms, $R^2$ and $R^3$, independently of one another, represent an alkyl group containing from 1 to 16 carbon atoms, or a group corresponding to $CH_2CH_2OR^5$, $R^4$ is an alkyl group containing from 1 to 4 carbon atoms, $R^5$ is hydrogen and/or $R^1CO$, and X is an anion; is disclosed.

8 Claims, No Drawings

USE OF QUATERNARY CARBOXYLIC ACID ALKANOLAMINE ESTER SALTS AS MICROBICIDE AGENTS

BACKGROUND OF THE INVENTION

Microbicidal agents are generally used to stop microorganisms from proliferting or to destroy them altogether. Hitherto, quaternary ammonium compounds, such as benzalkonium chloride or cetyl trimethyl ammonium chloride, have been successfully used as microbicidal agents. Unfortunately, it has been found that such compounds are not readily biodegradable in sewage treatment plants. Accordingly, there is a need for microbicidal compounds which are comparable in their performance with the quaternary ammonium compounds, but which have distinctly improved biological degradability.

U.S. Pat. No. 3,910,971 describes quaternary carboxylic acid alkanolamine ester salts obtainable by reaction of 2-dimethylamino-2-methyl-1-propanol with fatty acids and subsequent quaternization as microbicidal agents. However, these compounds are largely ineffectual against the gram-negative bacterium Pseudomonas aeruginosa which is a disadvantage in view of the commonly occurring waterborne germ which leads above all to product contamination.

European patent application EP 0 461 419 describes poly(oxy-1alkylene)aminoalkanol esters and ammonium compounds thereof which are also said to show microbicidal activity. However, these compounds have to contain at least one hydroxyisopropyl group and bear a methyl group at the nitrogen atom. No mention is made of the effectiveness of these compounds against bacteria, particularly against the commonly occurring bacterium Pseudomonas aeruginosa.

The problem addressed by the present invention was to provide microbicidal compounds which would be comparable in their microbicidal activity with conventional quaternary ammonium compounds. Above all, the compounds would also be microbicidally active against the commonly occurring bacterium Pseudomonas aeruginosa. In addition, the compounds would show better biodegradability than the conventional quaternary ammonium compounds.

BRIEF SUMMARY OF THE INVENTION

The present invention includes the use of quaternary carboxylic acid alkanolamine ester salts as microbicidal agents, more particularly in detergents, disinfectants, preservatives, fabric softeners, cosmetics, cooling lubricant emulsions and in coating compositions. The present invention also relates to detergents, fabric softeners, disinfectants, preservatives, cosmetics, cooling lubricant emulsions and coating compositions containing these quaternary carboxylic acid alkanolamine ester salts.

It has been found that special quaternary carboxylic acid alkanolamine ester salts satisfy this requirement.

Accordingly, the present invention relates to the use of quaternary carboxylic acid alkanolamine ester salts corresponding to general formula (I):

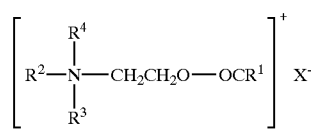
(I)

in which $R^1CO$ is an acyl group containing 2 to 18 carbon atoms, $R^2$ and $R^3$ independently of one another represent an alkyl group containing 1 to 16 carbon atoms or a group with the formula $CH_2—CH_2—O—R^5$, $R^4$ is an alkyl group containing 1 to 4 carbon atoms, $R^5$ is hydrogen and/or $R^1CO$ and $X^-$ is an anion, as microbicidal agents.

DETAILED DESCRIPTION OF THE INVENTION

The quaternary carboxylic acid alkanolamine ester salts are compounds known from the literature which are often also referred to as "esterquats". They are generally prepared by esterification of the alkanolamines with carboxylic acids in the presence of hypophosphorous acid, passing air through the reaction mixture and then quaternizing the esterification product. U.S. Pat. Nos. 3,915,867, 4,370,272, EP-A0 239 910, EP-A-0 293 955, EP-A0 295 739 and EP-A-0 309 052 are cited here are representative of the abundant prior art available on the subject.

According to the invention, the quaternary carboxylic acid alkanolamine ester salts are prepared by methods known per se, alkanolamines corresponding to formula (II):

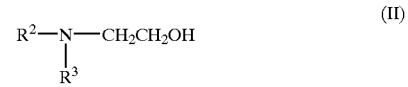
(II)

in which $R^2$ and $R^3$ are as defined for formula (I), with the proviso that, where $R^2$ and/or $R^3$ represent(s) the group $CH_2CH_2OR^5$, $R^5$ is hydrogen, being esterified with carboxylic acids corresponding to the formula $R^1COOH$. The alkanolamines corresponding to formula (II) may also be transesterified with esters of the described carboxylic acids to give the compounds of formula (I) used in accordance with the invention. Suitable alkanolamines are dialkyl ethanolamines ($R^2$, $R^3$=alkyl group containing 1 to 16 carbon atoms), such as dimethyl ethanolamine, methylethyl ethanolamine, diethyl ethanolamine, methylbutyl ethanolamine and/or methylhexyl ethanolamine, monoalkyl diethanolamines ($R^2$=$CH_2CH_2OH$; $R^3$=$C_{1-16}$ alkyl group), such as methyl diethanolamine, ethyl diethanolamine and/or butyl diethanolamine, and/or triethanolamines ($R^2$, $R^3$=$CH_2CH_2OH$). Monoalkyl diethanolamines and/or triethanolamines are preferably used.

Suitable carboxylic acids $R^1COOH$ are aliphatic saturated and/or unsaturated carboxylic acids, more particularly aliphatic saturated carboxylic acids, such as acetic acid, propionic acid, butyric acid, caproic acid, caprylic acid, capric acid, pelargonic acid, lauric acid, myristic acid, palmitic acid and the technical mixtures thereof obtained, for example, in the pressure hydolysis of natural fats and oils. Aliphatic saturated carboxylic acids containing 8 to 12 carbon atoms are preferred so that $R^1CO$ in formula (I) is preferably an aliphatic saturated acyl group containing 8 to 12 carbon atoms.

The quantity ratio of carboxylic acids or carboxylic acid esters to the alkanolamines is determined by the required degree of esterification of the free hydroxyl groups of the alkanolamines. In the case of the preferred monoalkyl diethanolamines and triethanolamine, all or only some of the free hydroxyl groups can be esterified with the carboxylic acids. If the hydroxyl group is not esterified, $R^5$ in general formula (I) stands for $R^1CO$. The esterification may be complete or partial. Where esterification is partial, the average degree of esterification of the—overall—free hydroxyl groups in the case of the monoalkyl diethanolamines is preferably in the range from 1.2 to 1.7 and, in the case of the triethanolamines, is preferably in the range from 1.2 to 2.5, i.e. mixtures of mono-, di- and optionally triesters of the di- or triethanolamines with carboxylic acids are present. According to the invention, at least two of the free hydroxyl groups in the triethanolamine are esterified with carboxylic acids. Instead of the carboxylic acids, ester derivatives thereof with the alkanolamines may also be reacted.

The subsequent quaternization is carried out by the methods known in this field and leads to the quaternary carboxylic acid alkanolamine ester salts corresponding to general formula (I). Compounds with the formula $R^4X$, where $R^4$ is as defined for formula (I) and preferably stands for a methyl group, are used for the quaternization. Where X in general formula (I) stands for formate, acetate, tartrate, dicarboxylate, citrate, halide, sulfate or nitrate, the usual quaternization was followed by an anion exchange.

According to the invention, it is particularly preferred to use compounds of formula (I) in which $R^2$ is a group $CH_2CH_2OR^5$ and $R^3$ is a methyl group and/or in which $R^2$ and $R^3$ stand for a group $CH_2CH_2OR^5$ where $R^5$ is as previously defined. Examples of particularly suitable compounds are dimethyl diethanolammonium dicaprylic acid ester methosulfate, methyl triethanolammonium tricaprylic acid ester methosulfate, methyl triethanolammonium dicaprylic acid ester methosulfate and dimethyl diethanolammonium dipelargonic acid ester methosulfate.

According to the invention, the described compounds are used as microbicidal agents. In the context of the invention, microbicidal agents are understood to be chemicals which are capable of destroying, or preventing the proliferation of, bacteria, yeasts, fungi, viruses and protists.

Microbicidal agents corresponding to this definition may be used in any products where a corresponding effect is required. They are preferably used in detergents/cleaners, for example in manual dishwashing detergents, multipurpose cleaners, sanitary cleaners, fabric softeners for the antimicrobial finishing of textiles, in disinfectants, for example in the home and in hospitals, in preservatives, for example for preserving industrial raw materials and products, in cooling lubricant emulsions, in cosmetics and in coating compositions, such as glues, paints and wood preservatives.

The compounds used in accordance with the invention are effective against bacteria in quantities of only >5 mg/l, expressed as active substance and based on the particular preparation. They are generally used in quantities of 5 to 5,000 mg/l and preferably in quantities of 50 to 1,000 mg/l, expressed as active substance and based on the particular preparation. In the case of concentrates, the quaternary carboxylic acid alkanolamine ester salts may also be used in larger quantities. However, if the concentrates are diluted with water by the end user, the quantities used are again in the range mentioned above.

The compounds used in accordance with the invention may be used in pure form or in the form of solutions. Suitable solvents are water and/or lower alcohols, more particularly ethanol, propanediol and/or isopropanol. Lower alcohols or aqueous mixtures thereof are recommended above all for quaternary carboxylic acid alkanolamine ester salts of the described type which contain more than two acyl groups bearing more than 6 carbon atoms.

The present invention also relates to detergents/cleaners containing quaternary carboxylic acid alkanolamine ester salts as microbicidal agents, to preservatives containing quaternary carboxylic acid alkanolamine ester salts as microbicidal agents, to cosmetics containing quaternary carboxylic acid alkanolamine ester salts as microbicidal agents, to disinfectants containing quaternary carboxylic acid alkanolamine ester salts, to cooling lubricant emulsions containing quaternary carboxylic acid alkanolamine ester salts and to fabric softeners containing quaternary carboxylic acid alkanolamine ester salts as microbicidal agents. The quaternary carboxylic acid alkanolamine ester salts may be present in such preparations in the quantities mentioned above. In addition, the preparations may of course also contain other microbicidal agents and other typical ingredients in typical quantities.

Thus, the following anionic, nonionic and/or amphoteric or zwitterionic surfactants, for example, may be present in the detergents/cleaners:

Anionic surfactants: alkyl benzenesulfonates, alkanesulfonates, olefin sulfonates, alkyl ether sulfonates, glycerol ether sulfonates, methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, sulfosuccinates, sulfosuccinamates, sulfotriglycerides, ether carboxylic acids, alkyl oligoglucoside sulfates, alkyl (ether) phosphates and protein fatty acid condensates. Nonionic surfactants: fatty alcohol polyglycol ethers, alkyl phenol polyglycol ethers, fatty amine polyglycol ethers, fatty acid amide polyglycol ethers, fatty acid polyglycol esters, alkoxylated triglycerides, alkyl oligoglycosides, sugar esters, sorbitan esters, polysorbates, polyol fatty acid esters, amine oxides, fatty acid alkanolamides, alkyl lactams and fatty acid-N-alkyl glucamides. Amphoteric or zwitterionic surfactants: alkylamidobetaines, aminopropionates, aminoglycinates, imidazolinium betaines and sulfobetaines.

The detergents/cleaners may also contain typical ingredients, such as builders, salts, bleaching agents, optical brighteners, redeposition inhibitors, solubilizers and enzymes.

The preservatives may contain alcohols, aldehydes, acids, esters, phenols, terpenes and/or complexing agents.

The disinfectants may also contain one or more of the above-mentioned anionic, nonionic and/or amphoteric or zwitterionic surfactants and also water, alcohols, complexing agents and other microbicidal compounds.

The cooling lubricant emulsions generally contain an aqueous phase and an organic phase, the organic phase generally being formed by mineral oils or vegetable oils. In addition, emulsifiers, optionally extreme pressure additives, corrosion inhibitors and/or complexing agents are mostly present.

The cosmetics may also contain one or more of the above-mentioned anionic, nonionic and/or amphoteric or zwitterionic surfactants and optionally water or a water phase, alcohols, optionally an oil phase, emulsifiers and optionally other microbicidal compounds. Typical additives, such as abrasives, pearlizing pigments, dyes, perfumes, optionally other preservatives, gel formers and/or conditioning and care principles, may be present

EXAMPLES

A. Microbicidal Activity

The microbicidal activity of the quanterary carboxylic acid alkanolamine ester salts used in accordance with the invention was tested against the following selected test germs:

a) *Staphylococcus aureus* ATCC 6538
b) *Pseudomonas aeruginosa* ATCC 15442
c) *Candida albicans* ATCC 10231

The effectiveness of the compound to be tested was determined by the suspension test in accordance with the guidelines of the Deutsche Gesellschaft for Hygiene and Mikrobiologie (DGHM). Test solutions containing quaternary carboxylic acid alkanolamine ester salts in the quantities shown in the Tables of 50, 100, 200, 400 and 800 mg/l were prepared using water with a hardness of 17° dH and optionally isopropanol.

At room temperatures, quantities of 0.1 ml test germ suspension were pipetted into test tubes containing 10 ml of the test solutions described above and mixed. After various contact times of 5, 15, 30 and 60 minutes, 1 ml of material was taken from the test tubes by pipette and transferred to 9 ml inactivator solution (inactivators: 3.0% Tween, 0.3% lecithin, 0.1% histidine). After in activation for at least 5 and at most 30 minutes, the living germ count was determined by plating out onto casein peptone-soybean flour peptone (CaSo)-agar plates. Using a spiral plater, the inactivating mixture was directly plated out onto CaSo-agar. The samples were incubated for 24 to 72 hours at 37° C. and macroscopically evaluated for growth. The destruction time or the residual germ count was determined in this way. The germ count of an unchallenged water control is related to the germ count of the inactivated test solution taking the dilution into account. The logarithmic reduction factors, i.e. the power of ten reduction, are shown in Table 1 below. The higher the value, the better the microbicidal effect. The symbol < means that the logarithmic reductuon factor is below the indicated value or, in the case of the symbol >, above the indicated value. The abbreviation CU stands for "concentration used".

The following compounds were tested:

Ex. 1: dimethyl diethanolammonium dicaprylic acid ester methosulfate
Ex 2: methyl triethanolammonium tricaprylic acid ester methosulfate
Ex. 3: dimethyl diethanolammonium dipelargonic acid ester methosulfate
Ex. 4: trimethyl ethanolammonium coconut fatty acid ester methosulfate
Ex. 5: methyl triethanolammonium dilauric acid ester methosulfate
Ex. 6: methyl triethanolammonium dicapric acid ester methosulfate
Ex. 7: methyl trethanolammonium dicaprylic acid ester methosulfate
Ex. 8: dimethyl diethanolammonium dilauric acid ester methosulfate
Ex. 9: methyl triethanolammonium tricapric acid ester methosulfate
Ex. 10: dimethyl diethanolammonium dicapric acid ester methosulfate

TABLE 1

| | CU [mg/l] | | | | |
|---|---|---|---|---|---|
| | 50 | 100 | 200 | 400 | 800 |

Example 1:
Dimethyl diethanolammonium dicaprylic acid ester methosulfate

Staphylococcus aureus ATCC 6538
Germ count 2.73 · 10$^7$/ml

| | 50 | 100 | 200 | 400 | 800 |
|---|---|---|---|---|---|
| 5 mins. | <1.32 | <1.32 | <1.32 | <1.32 | <1.32 |
| 15 mins. | <1.71 | <1.71 | <1.71 | <1.1 | <3.59 |
| 30 mins. | <1.23 | <1.23 | <1.23 | 1.95 | <3.96 |
| 60 mins. | <1.32 | <1.32 | <1.32 | 3.54 | >5.32 |

TABLE 1-continued

| | CU [mg/l] | | | | |
|---|---|---|---|---|---|
| | 50 | 100 | 200 | 400 | 800 |

Pseudomonas aeruginosa ATCC 15442
Germ count 4.23 · 10$^7$/ml

| | 50 | 100 | 200 | 400 | 800 |
|---|---|---|---|---|---|
| 5 mins. | <1.83 | <1.83 | <1.83 | <1.83 | >5.83 |
| 15 mins. | <1.47 | <1.47 | <1.47 | <1.47 | >5.47 |
| 30 mins. | <1.55 | <1.55 | <1.55 | 3.22 | >5.55 |
| 60 mins. | <1.56 | <1.56 | <1.56 | 4.41 | >5.56 |

Candida albicans ATCC 10231
Germ count 2.59 · 10$^6$/ml

| | 50 | 100 | 200 | 400 | 800 |
|---|---|---|---|---|---|
| 5 mins. | <0.50 | <0.50 | 1.53 | >4.5 | >4.50 |
| 15 mins. | <0.37 | 0.41 | 2.53 | >4.37 | >4.37 |
| 30 mins. | <0.35 | 0.60 | 2.91 | >4.35 | >4.35 |
| 60 mins. | <0.36 | 0.70 | 3.61 | >4.36 | >4.36 |

Example 2:
Methyl triethanolammonium tricaprylic acid ester methosulfate

Staphylococcus aureus ATCC 6538
Germ count 1.44 · 10$^7$/ml

| | 50 | 100 | 200 | 400 | 800 |
|---|---|---|---|---|---|
| 5 mins. | 3.21 | 3.54 | 4.32 | >5.56 | >5.56 |
| 15 mins. | >5.38 | >5.38 | >5.38 | >5.38 | >5.38 |
| 30 mins. | >5.50 | >5.50 | >5.50 | >5.50 | >5.50 |
| 60 mins. | >5.41 | >5.41 | >5.41 | >5.41 | >5.41 |

Pseudomonas aeruginosa ATCC 15442
Germ count 6.27 · 10$^7$/ml

| | 50 | 100 | 200 | 400 | 800 |
|---|---|---|---|---|---|
| 5 mins. | <1.38 | <1.38 | 1.38 | 4.08 | 4.42 |
| 15 mins. | <1.70 | 3.25 | 3.95 | >5.70 | >5.70 |
| 30 mins. | 3.31 | 3.75 | 4.40 | >5.68 | >5.68 |
| 60 mins. | 3.98 | 4.49 | >5.59 | >5.59 | >5.59 |

Candida albicans ATCC 10231
Germ count 6.91 · 10$^6$/ml

| | 50 | 100 | 200 | 400 | 800 |
|---|---|---|---|---|---|
| 5 mins. | 3.44 | >4.73 | >4.73 | >4.73 | >4.73 |
| 15 mins. | >4.71 | >4.71 | >4.71 | >4.71 | >4.71 |
| 30 mins. | >4.82 | >4.82 | >4.82 | >4.82 | <4.82 |
| 60 mins. | >4.68 | >4.68 | >4.68 | >4.68 | >4.68 |

Example 3:
Dimethyl diethanolammonium dipelargonic acid ester methosulfate

Staphylococcus aureus ATCC 6538
Germ count 2.41 · 10$^7$/ml

| | 50 | 100 | 200 | 400 | 800 |
|---|---|---|---|---|---|
| 5 mins. | <1.31 | <1.31 | 2.05 | 3.25 | 3.78 |
| 15 mins. | 2.31 | 3.67 | >5.74 | >5.74 | >5.74 |
| 30 mins. | 3.01 | >5.19 | >5.19 | >5.19 | >5.19 |
| 60 mins. | 4.85 | >5.55 | >5.55 | >5.55 | >5.55 |

Pseudomonas aeruginosa ATCC 15442
Germ count 5.09 · 10$^7$/ml

| | 50 | 100 | 200 | 400 | 800 |
|---|---|---|---|---|---|
| 5 mins. | <1.59 | 4.36 | >5.59 | >5.59 | >5.59 |
| 15 mins. | 2.99 | >5.58 | >5.58 | >5.58 | >5.58 |
| 30 mins. | 3.58 | >5.67 | >5.67 | >5.67 | >5.67 |
| 60 mins. | 3.77 | >5.53 | >5.53 | >5.53 | >5.53 |

Candida albicans ATCC 10231
Germ count 4.82 · 10$^6$/ml

| | 50 | 100 | 200 | 400 | 800 |
|---|---|---|---|---|---|
| 5 mins. | 2.86 | >4.63 | >4.63 | >4.63 | >4.63 |
| 15 mins. | >4.63 | >4.63 | >4.63 | >4.63 | >4.63 |
| 30 mins. | >4.66 | >4.66 | >4.66 | >4.66 | >4.66 |
| 60 mins. | >4.67 | >4.67 | >4.67 | >4.67 | >4.67 |

Example 4:
Trimethyl ethanolammonium coconut fatty acid ester methosulfate 75% in isopropanol Staphylococcus aureus ATCC 6538
Germ count 2.05 · 10$^7$/ml

| | 50 | 100 | 200 | 400 | 800 |
|---|---|---|---|---|---|
| 5 mins. | <1.51 | <1.51 | <1.51 | 2.33 | 3.12 |
| 15 mins. | <1.36 | 1.78 | 3.4 | 4.14 | >5.36 |
| 30 mins. | <1.38 | 3.03 | 4.38 | >5.38 | >5.38 |
| 60 mins. | 1.94 | 4.02 | >5.26 | >5.26 | >5.26 |

TABLE 1-continued

| | \multicolumn{5}{c}{CU [mg/l]} | | | | |
|---|---|---|---|---|---|
| | 50 | 100 | 200 | 400 | 800 |

*Pseudomonas aeruginosa* ATCC 15442
Germ count 5.77 · 10⁷/ml

| | | | | | |
|---|---|---|---|---|---|
| 5 mins. | <1.51 | <1.51 | <1.51 | <1.51 | 4.02 |
| 15 mins. | <1.66 | <1.66 | <1.66 | 3.9 | >5.66 |
| 30 mins. | <1.46 | <1.46 | <1.46 | >5.66 | >5.66 |
| 60 mins. | <1.47 | <1.47 | <1.47 | <3.35 | >5.47 |

*Candida albicans* ATCC 10231
Germ count 7.05 · 10⁷/ml

| | | | | | |
|---|---|---|---|---|---|
| 5 mins. | <0.80 | 1.19 | 3.43 | >4.80 | >4.80 |
| 15 mins. | <0.79 | 3.01 | >4.79 | >4.79 | >4.79 |
| 30 mins. | 0.91 | >4.80 | >4.80 | >4.80 | >4.80 |
| 60 mins. | 1.40 | >5.05 | >5.05 | >5.05 | >5.05 |

Example 5:
Methyl triethanolammonium dilauric acid ester methosulfate

*Staphylococcus aureus* ATCC 6538
Germ count 5.95 · 10⁹/ml

| | | | | | |
|---|---|---|---|---|---|
| 5 mins. | <1.79 | <1.79 | 2.52 | 2.70 | 3.85 |
| 15 mins. | <1.73 | 2.38 | 4.25 | >5.73 | >5.73 |
| 30 mins. | 2.53 | 3.80 | >5.75 | >5.75 | >5.75 |
| 60 mins. | 3.88 | 5.21 | >5.86 | >5.86 | >5.86 |

*Pseudomonas aeruginosa* ATCC 15442
Germ count 7.86 · 10⁹/ml

| | | | | | |
|---|---|---|---|---|---|
| 5 mins. | <1.85 | <1.85 | <1.85 | <1.85 | <1.85 |
| 15 mins. | <1.79 | <1.79 | <1.79 | <1.79 | 3.43 |
| 30 mins. | <1.71 | <1.71 | <1.71 | <1.71 | 3.95 |
| 60 mins. | <1.51 | <1.81 | <1.81 | 3.84 | 4.40 |

Example 6:
Methyl triethanolammonium dicapric acid ester methosulfate

*Staphylococcus aureus* ATCC 6538
Germ count 5.95 · 10⁹/ml

| | | | | | |
|---|---|---|---|---|---|
| 5 mins. | 4.12 | 4.58 | 4.55 | 4.48 | 5.44 |
| 15 mins. | >5.73 | >5.73 | >5.75 | >5.75 | >5.73 |
| 30 mins. | >5.75 | >5.75 | >5.75 | >5.75 | >5.75 |
| 60 mins. | >5.86 | >5.86 | >5.86 | >5.86 | >5.86 |

*Pseudomonas aeruginosa* ATCC 15442
Germ count 7.86 · 10⁹/ml

| | | | | | |
|---|---|---|---|---|---|
| 5 mins. | <1.85 | <1.85 | <1.85 | <1.85 | <1.85 |
| 15 mins. | <1.79 | <1.79 | <1.79 | <1.79 | 4.14 |
| 30 mins. | <1.71 | <1.71 | 3.35 | 4.18 | 4.76 |
| 60 mins. | <1.81 | 3.19 | 3.89 | >5.81 | >5.81 |

*Candida albicans* ATCC 10231
Germ count 8.95 · 10⁸/ml

| | | | | | |
|---|---|---|---|---|---|
| 5 mins. | <0.87 | 1.27 | 1.24 | 1.38 | 1.33 |
| 15 mins. | 1.64 | 3.03 | 3.66 | 3.51 | >4.87 |
| 30 mins. | 1.93 | 3.75 | >4.78 | >4.78 | >4.78 |
| 60 mins. | 2.62 | 4.15 | >4.67 | >4.67 | >4.67 |

Example 7:
Methyl triethanolammonium dicaprylic acid ester methosulfate

*Staphylococcus aureus* ATCC 6538
Germ count 3.5 · 10⁹/ml

| | | | | | |
|---|---|---|---|---|---|
| 5 mins. | >5.75 | >5.75 | >5.75 | >5.75 | >5.75 |
| 15 mins. | >5.53 | >5.53 | >5.53 | >5.53 | >5.53 |
| 30 mins. | >5.42 | >5.42 | >5.42 | >5.42 | >5.42 |
| 60 mins. | >5.69 | >5.69 | >5.69 | >5.69 | >5.69 |

*Pseudomonas aeruginosa* ATCC 15442
Germ count 9.14 · 10⁹/ml

| | | | | | |
|---|---|---|---|---|---|
| 5 mins. | <1.77 | 3.64 | 4.59 | 5.32 | >5.77 |
| 15 mins. | <1.72 | >5.72 | >5.72 | >5.72 | >5.72 |
| 30 mins. | <1.76 | >5.76 | 5.76 | >5.76 | >5.76 |
| 60 mins. | 3.65 | >5.86 | >5.86 | >5.86 | >5.86 |

TABLE 1-continued

| | \multicolumn{5}{c}{CU [mg/l]} | | | | |
|---|---|---|---|---|---|
| | 50 | 100 | 200 | 400 | 800 |

*Candida albicans* ATCC 10231
Germ count 1.81 · 10⁸/ml

| | | | | | |
|---|---|---|---|---|---|
| 5 mins. | >4.31 | >4.31 | >4.31 | >4.31 | >4.31 |
| 15 mins. | >4.18 | >4.18 | >4.18 | >4.18 | >4.18 |
| 30 mins. | >4.16 | >4.16 | >4.16 | >4.16 | >4.16 |
| 60 mins. | >4.27 | >4.27 | >4.27 | >4.27 | >4.27 |

Example 8:
Dimethyl diethanolammonium dilauric acid ester methosulfate

*Staphylococcus aureus* ATCC 6538
Germ count 4.23 · 10⁹/ml

| | | | | | |
|---|---|---|---|---|---|
| 5 mins. | | | <1.39 | 1.98 | 2.34 |
| 15 mins. | | | 3.24 | 3.40 | 4.64 |
| 30 mins. | | | 4.28 | 5.29 | >5.51 |
| 60 mins. | | | 4.23 | >5.60 | >5.60 |

*Pseudomonas aeruginosa* ATCC 15442
Germ count 8.5 · 10⁹/ml

| | | | | | |
|---|---|---|---|---|---|
| 5 mins. | | | <1.88 | <1.88 | <1.88 |
| 15 mins. | | | <1.93 | <1.93 | <1.93 |
| 30 mins. | | | <1.80 | <1.80 | 3.05 |
| 60 mins. | | | <1.90 | 3.05 | 3.77 |

Example 9:
Methyl triethanolammonium tricapric acid ester methosulfate

*Staphylococcus aureus* ATCC 6538
Germ count 4.23 · 10⁹/ml

| | | | | | |
|---|---|---|---|---|---|
| 5 mins. | | | <1.39 | <1.39 | <1.39 |
| 15 mins. | | | <1.59 | <1.59 | <1.59 |
| 30 mins. | | | <1.51 | <1.51 | 1.83 |
| 60 mins. | | | <1.60 | 2.09 | 2.97 |

*Pseudomonas aeruginosa* ATCC 15442
Germ count 8.5 · 10⁹/ml

| | | | | | |
|---|---|---|---|---|---|
| 5 mins. | | | <1.88 | <1.88 | <1.88 |
| 15 mins. | | | <1.93 | <1.93 | <1.93 |
| 30 mins. | | | <1.80 | <1.80 | 3.27 |
| 60 mins. | | | <1.90 | 2.94 | 3.72 |

Example 10:
Dimethyl diethanolammonium dicapric acid ester methosulfate

*Staphylococcus aureus* ATCC 6538
Germ count 5.95 · 10⁹/ml

| | | | | | |
|---|---|---|---|---|---|
| 5 mins. | | | >5.56 | >5.56 | >5.56 |
| 15 mins. | | | >5.55 | >5.55 | >5.55 |
| 30 mins. | | | >5.72 | >5.72 | >5.72 |
| 60 mins. | | | >5.69 | >5.69 | >5.69 |

*Pseudomonas aeruginosa* ATCC 15442
Germ count 9.45 · 10⁹/ml

| | | | | | |
|---|---|---|---|---|---|
| 5 mins. | | | 3.11 | 3.54 | 4.31 |
| 15 mins. | | | 3.48 | 4.51 | 5.04 |
| 30 mins. | | | 3.95 | 5.50 | 5.64 |
| 60 mins. | | | 4.84 | 5.44 | >5.79 |

*Candida albicans* ATCC 10231
Germ count 1.03 · 10⁹/ml

| | | | | | |
|---|---|---|---|---|---|
| 5 mins. | | | 2.87 | 4.27 | |
| 15 mins. | | | >4.84 | >4.84 | |
| 30 mins. | | | >4.89 | >4.89 | |
| 60 mins. | | | >4.80 | >4.80 | |

B. Microbicidal Activity Against Other Bacteria and Fungi

Methyl triethanolammonium dioctanoic acid ester methosulfate was tested as in A) against the bacteria
*Salmonella enteritidis*
*Escherichia coli*
*Enterococcus faecium*
and the fungi
*Microsporum gypseum*
*Trichophyton mentagrophytes*

The logarithmic reduction rates of Example 11 are shown in Table 2.

TABLE 2 for Example 11 Results

| | 50 ppm | 100 ppm | 200 ppm | 400 ppm |
|---|---|---|---|---|
| Fungi | | | | |
| *Microsporum gypseum* | | | | |
| 5 Mins. | >3.52 | >3.52 | >3.52 | >3.52 |
| Water control GERM COUNT/ml: 3.31 × 10⁴ | | | | |
| 15 Mins. | >3.58 | >3.58 | >3.58 | >3.58 |
| Water control GERM COUNT/ml: 3.80 × 10⁴ | | | | |
| 60 Mins. | >3.62 | >3.62 | >3.62 | >3.62 |
| Water control GERM COUNT/ml: 4.17 × 10⁴ | | | | |
| *Trichophyton mentagrophytes* | | | | |
| 5 Mins. | 0.34 | 0.38 | 0.28 | 0.35 |
| Water control GERM COUNT/ml: 7.59 × 10⁴ | | | | |
| 15 Mins. | 0.95 | 0.95 | 0.92 | 0.89 |
| Water control GERM COUNT/ml: 6.76 × 10⁴ | | | | |
| 60 Mins. | 2.04 | 2.05 | 2.16 | 2.29 |
| Water control GERM COUNT/ml: 7.24 × 10⁴ | | | | |
| Bacteria | | | | |
| *Salmonella Enteritidis* | | | | |
| 5 Mins. | <1.8 | 3.96 | 4.88 | >5.8 |
| Water control GERM COUNT/ml: 6.31 × 10⁶ | | | | |
| 15 Mins. | 3.29 | 5.12 | >5.77 | >5.72 |
| Water control GERM COUNT/ml: 5.89 × 10⁶ | | | | |
| 60 Mins. | 3.67 | >5.76 | >5.76 | >5.76 |
| Water control GERM COUNT/ml: 5.75 × 10⁶ | | | | |
| *Escherichia coli* | | | | |
| 5 Mins. | 4.12 | >5.58 | >5.58 | >5.58 |
| Water control GERM COUNT/ml: 3.8 × 10⁶ | | | | |
| 15 Mins. | >5.62 | >5.62 | >5.62 | >5.62 |
| Water control GERM COUNT/ml: 4.17 × 10⁶ | | | | |
| 60 Mins. | >5.76 | >5.76 | >5.76 | >5.76 |
| Water control GERM COUNT/ml: 5.75 × 10⁶ | | | | |
| *Enterococcus faecium* | | | | |
| 5 Mins. | >6.3 | >6.3 | >6.3 | >6.3 |
| Water control GERM COUNT/ml: 2 × 10⁷ | | | | |
| 15 Mins. | >5.88 | >5.88 | >5.88 | >5.88 |
| Water control GERM COUNT/ml: 7.59 × 10⁶ | | | | |
| 60 Mins. | >5.96 | >5.96 | >5.96 | >5.96 |
| Water control GERM COUNT/ml: 9.12 × 10⁶ | | | | |

The effectiveness against bacteria was confirmed by the test results obtained. The compositions were found to be particularly effective against gram-positive bacteria.

The fungus *Microsporum gypseum* is almost completely killed off by a concentration of 50 mg/l, even after the shortest contact time. Against the dermatophyte *Trichophyton mentagrophytes*, the beginnings of activity with a destruction of around 2 powers of ten are observed at least after a long contact time (60 minutes).

What is claimed is:

1. A process for destroying or preventing the proliferation of microorganisms, said process comprising contacting a microorganism with a quaternary carboxylic acid alkanolamine ester salt of the general formula (I):

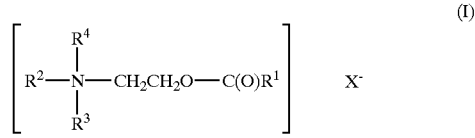

wherein $R^1CO$ represents an acyl group having from about 2 to about 18 carbon aroms, $R^2$ and $R^3$ each independently represent an aly group having from about 1 to about 16 carbon atoms, or a group corresponding to $CH_2CH_2OR^5$, wherein at least one of $R^2$ and $R^3$ represents a group corresponding to $CH_2CH_2OR^5$, $R^4$ represents an allyl group having from about 1 to about 4 carbon atoms, each $R^5$ independently represents a substituent selected from the group consisting of a bydrogen atom and $R^1CO$, and X represents an anion.

2. The process according to claim 1, wherein $R^1CO$ represents an aliphatic saturated acyl group having form about 8 to about 12 carbon atoms.

3. The process according to claim 1, wherein $R^2$ represents a group corresponding to $CH_2CH_2OR^5$ and $R^3$ represents a methyl group.

4. The process according to claim 1, wherein each of $R^2$ and $R^3$ represents a group corresponding to $CH_2CH_2OR^5$.

5. The process according to claim 1, wherein $R^2$ represents $CH_2CH_2OOCR^1$ and $R^3$ represents $CH_2CH_2OR^5$.

6. The process according to claim 1, wherein each of $R^2$ and $R^3$ represents $CH_2CH_2OOCR^1$.

7. The process according to claim 1, wherein the quaternary carboxylic acid alkanolamine ester salt is present in a composition in an amount of from about 5 to about 5000 mg/l based on the total weight of the composition.

8. The process according to claim 1, wherein X represents an anion selected from the group consisting of methosulfate, ethosulfate, formate, acetate, tartrate, dicarboxylates, citrate, halides, sulfate, phosphate and nitrate.

* * * * *